United States Patent [19]

Cabuz

[11] Patent Number: 5,836,750
[45] Date of Patent: Nov. 17, 1998

[54] ELECTROSTATICALLY ACTUATED MESOPUMP HAVING A PLURALITY OF ELEMENTARY CELLS

[75] Inventor: Cleopatra Cabuz, Edina, Minn.

[73] Assignee: Honeywell Inc., Minneapolis, Minn.

[21] Appl. No.: 947,802

[22] Filed: Oct. 9, 1997

[51] Int. Cl.$^6$ .................................................. F04B 35/00
[52] U.S. Cl. .................. 417/322; 417/413.1; 417/413.3; 417/62
[58] Field of Search .............................. 417/322, 413.1, 417/413.3, 62

[56] References Cited

U.S. PATENT DOCUMENTS

| | | | |
|---|---|---|---|
| 3,381,623 | 5/1968 | Elliot | 103/152 |
| 3,803,424 | 4/1974 | Smiley et al. | 307/149 |
| 4,115,036 | 9/1978 | Paterson | 417/322 |
| 4,453,169 | 6/1984 | Martner | 346/140 PD |
| 4,498,850 | 2/1985 | Perlov et al. | 417/322 |
| 4,938,742 | 7/1990 | Smits | 604/67 |
| 5,078,581 | 1/1992 | Blum et al. | 417/322 |
| 5,096,388 | 3/1992 | Weinberg | 417/322 |
| 5,176,358 | 1/1993 | Bonne . | |
| 5,180,288 | 1/1993 | Richter et al. | 417/48 |
| 5,192,197 | 3/1993 | Culp | 417/322 |
| 5,499,909 | 3/1996 | Yamada et al. | 417/384 |
| 5,725,363 | 3/1998 | Bustgens et al. | 417/413.1 |
| 5,759,014 | 6/1998 | Van Lintel | 417/413.3 |
| 5,759,015 | 6/1998 | Van Lintel et al. | 417/322 |

OTHER PUBLICATIONS

Cabuz, "Tradeoffs in MEMS Materials", SPIE vol. 2881, p.160 (Oct. 1996).
Bertz,Schubert, Werner, "Silicon Grooves with Sidewall Angles down to 1° made by Dry Etching".
Bustgens,Bacher,Menz,Schomburg, "Micropump Manufactured by Thermoplastic Molding" MEMS 1994.
Wagner,Quenzer, Hoerschelmann,Lisec,Juerss, "Bistable Microvalve with Pneumatically Coupled Membranes," 0–7803–2985–Jun. 1996 IEEE (1996).
Branebjerg,Gravesen "A New Electrostatic Actuator Providing Improved Stroke Length and Force," Micro Electro Mechanical Systems (Feb. 4–7, 1992).

*Primary Examiner*—Timothy Thorpe
*Assistant Examiner*—Ehud Gartenberg
*Attorney, Agent, or Firm*—John G. Shudy, Jr.

[57] ABSTRACT

A mesopump having a plurality of elementary cells and a method of pumping fluids using the mesopump. The cells each have a body forming a cavity having upper and lower electrodes with curved surfaces facing the other electrode. Electrical connections selectively energize the electrodes. A bistable diaphragm is mounted with its major portion located in the cavity between the electrodes so that the diaphragm deflects toward the upper or lower surfaces to conform thereto. A lateral conduit is located at at least one end of the body for fluid communication with the cavity. The lateral conduits are operably connected to a portion of the diaphragm mounted in the body and are opened and closed by movement of the diaphragm. A vertical conduit on at least one curved surface controls flow of fluid by movement of the diaphragm into and out of contact with the vertical conduit. The cells are interconnected to form the mesopump whereby activation of the electrodes causes movement of the diaphragm between the electrodes to move fluid into and out of the body. The preferred mesopump includes sets of three cell groups so that fluid enters a first cell from a source of fluid, is expelled to a second cell through a vertical conduit; expelled via a lateral conduit to a third cell, and expelled therefrom, whereby fluid passes from cell to cell upon activation of the electrodes.

17 Claims, 3 Drawing Sheets

Shallow Channel in chamber #2

ELECTROSTATICALLY ACTUATED MESOPUMP HAVING A PLURALITY OF ELEMENTARY CELLS

The U.S. Government may have certain rights to the present invention.

FIELD OF THE INVENTION

The present invention relates to a mesoscopic pump. More particularly the invention relates to a mesoscopic pump based upon bistable electrostatically activated diaphragm arrays.

BACKGROUND OF THE INVENTION

Modern industrial, commercial, aerospace and military systems depend critically on reliable pumps for fluid handling. The trends in fluid handling systems are toward smaller, more distributed and more portable systems for increasing uses in instrumentation and control.

Although important advances in pump technology have been made in the past few decades, progress has reached saturation in terms of ability to reduce pump size, weight and power requirements. There is a significant gap between the technology for conventional pumps, including the so-called "micropumps," and MEMS pumps that are based on silicon micromachining and microelectronics technology.

The pumping capability of MEMS pumps is placed in the microliters to tens of milliliters per minute range. This makes them useful for applications such as implantable systems for drug delivery or micro dosage in chemical analysis systems but such pumping speeds are many orders of magnitude smaller than those required in sampling applications.

Conventional pumps that are commercially available have capacities that range from tenths of a liter per minute to several hundreds of liters per minute. Most of these pumps require large amounts of power. Even the smaller pumps are typically in the size range of 10–50 cubic inches. There are also commercially available micropumps that operate with lower input power, but have capacities below one liter per minute.

A number of United States patents have been granted on apparatus and devices generally relating to microvalve construction and control. For example, U.S. Pat. No. 5,082,242 to Bonne et al describes a microvalve that is an integral structure made on one piece of silicon such that the device is a flow through valve with inlet and outlet on opposite sides of the silicon wafer. The valves are closed by contact with a valve seat where surfaces must be matched in order to avoid degradation of valve performance. Two patents, U.S. Pat. Nos. 5,180,623 and 5,244,527 are divisional patents relating to the first mentioned patent.

Another family of patents describe fluid control employing microminiature valves, sensors and other components using a main passage between one inlet and exit port and additionally a servo passage between inlet and outlet ports. The servo passage is controlled by a control flow tube such that tabs are moved electrostatically. U.S. Pat. No. 5,176,358 to Bonne et al teaches such a fluid regulating device, while divisional U.S. Pat. Nos. 5,323,999 and 5,441,597 relate to alternative embodiments.

An additional concept is disclosed by Wagner et al in the June, 1996, edition of the IEEE Journal, pages 384–388, in which two buckled $Si/SiO_2$ membranes spanning air filled cavities having enclosed driving electrodes. A coupled membrane system is disclosed in which a first silicon membrane is switched by electrostatic force which, in turn, presses air through a channel to push the second silicon membrane up.

In both of these patented systems and in the concept described by Wagner et al, silicon semiconductor chips are employed. Silicon technology is, in fact, a host for a number of microsensors. The possibility of fabricating fully integrated systems led to the development of some of the above described valves and the like. However, the displacements available at the microscale and the materials available in silicon technology are not the best for such applications. The achievable pumping rates are very small ($\mu l$ to ml/min) at the best. Additionally the structures tent to become complicated and expensive. Of major concern also is the fact that silicon is not compatible with many biological materials, thus eliminating virtually an entire field of end use.

Current sampling pumps for vapor and particle detection are much larger than the instruments they support. In order to be effective for many missions, the sampling rate should be comparable to human breathing, i.e., 10 liters per minute (1 pm) or more. The pumps must supply this flow against pressure drops of one psi or more, corresponding to pneumatic output loads exceeding a watt and input power requirements exceeding ten watts. Current system using rotating motors are power hungry, noisy and have limited lifetimes. Mesoscopic pumps with no rotating or sliding parts and high electrical-to-pneumatic conversion efficiencies would be able to dramatically increase the capabilities and effectiveness of military systems that detect chemical, biological, explosive and other agents.

Use of silicon as a component for these systems has proven difficult, particularly in three areas. First, micromachining the desired curved surface in silicon is a problem; second the choice of materials is severely limited; and third, achieving the dimensions required for high pumping rates is almost impossible. Fabrication constraints result in a reduced radius of curvature at the supports, reduced travel of any diaphragm, and unidirectional actuation, all of which contribute to reduced pumping efficiency.

It would be a great advance in the art if a mesopump could be developed that would be able to supply pumping speeds and maximum pressures similar to conventional pressures at dimensions and power levels that are an order of magnitude smaller.

Another advantage would be if a mesopump would be available that used materials that are compatible with most, if not all, materials likely to be processed.

Other advantages will appear hereinafter.

SUMMARY OF THE INVENTION

It has now been discovered that the above and other objects of the present invention may be accomplished in the following manner. Specifically, the present invention provides a mesopump that comprises an array of elementary cells. Each cell includes a shaped chamber, a diaphragm and interconnecting conduits. The invention includes bistable diaphragms, bidirectional electrostatic activation with electrode cavities shaped to conform to the diaphragm deflection, a built in valve action that provides a strongly rectifying mechanism for flow of fluid, and serial connectability in a compact array.

The elementary cells are formed by a body with an electrode cavity having an upper electrode and a lower electrode, each having a curved surface facing toward the other electrode to define the cavity. The body includes a source of electrical activation for selectively energizing the electrodes. The bistable diaphragm is mounted and grounded in the body such that a major portion of the diaphragm is located in the cavity between the curved surfaces. The diaphragm deflects toward the upper and lower electrode curved surfaces to conform thereto when voltage is applied to the specific electrode and the grounded diaphragm.

Fluid enters and exits the cells via the pumping action of movement of the diaphragm from one electrode to the other. In some instances fluid flows through a lateral conduit at one or both ends of the body, acting as an inlet end conduit or an outlet end conduit for the cavity. The lateral conduits are each operably connected to the portion of the diaphragm mounted in the body so they may be opened and closed by movement of the diaphragm. In other instances fluid flows through vertical conduit means operatively connected to the curved surface of an electrode, and this flow is also controlled by movement of the diaphragm into and out of contact with the vertical conduit on that electrode curved surface. The cells are connected together to form units, whereby activation of the electrodes causes movement of the diaphragm between the curved surfaces of the electrodes to move fluid into and out of the mesopump.

The mesopump will normally further include a vertical back pressure control conduit on the opposite electrode and on the other side of the diaphragm from the vertical conduit.

In a preferred embodiment, the diaphragm is flexibly elastic to conform its surface area to the curved surfaces or the diaphragm is buckled to increase its surface area. When the diaphragm is flexibly elastic, it is formed from a polymeric material having elastomeric properties sufficient to permit movement between the curved surfaces.

Movement of the diaphragm from the curved surface of one electrode to the curved surface of the other electrode cooperates with the lateral conduit to open one of the inlet end conduit and outlet end conduit and closing the other of the inlet end conduit and outlet end conduit.

A preferred mesopump of this invention includes a plurality of sets of elementary cells that cooperatively function together. The set includes a first cell having an inlet end lateral conduit connected to a source of fluid and a fluid outlet formed by its vertical conduit means. The second cell is connected to the first cell vertical means by its vertical conduit, serving as its inlet source. Its outlet end lateral conduit serves as its fluid outlet to a third cell connected at its inlet end lateral conduit. The third cell fluid outlet is formed such that its outlet end lateral conduit means is its fluid outlet.

Movement of the various diaphragms upon application of appropriate voltage causes fluid to pass from cell to cell upon activation of the electrodes. In such a four cell array, a voltage is applied between a grounded diaphragm and an upper electrode of the first and second cells, whereby suction is created to cause fluid to enter through the first cell. Voltage is switched to the lower electrodes of the first and second cells, whereby fluid moves to the second cell. Switching voltage back to the upper electrode in the second cell and applying voltage to the upper electrode in the third cell causes fluid to transfer through the second cell outlet into the third cell through the third cell. Applying a voltage between a grounded diaphragm and an upper electrode of the third cell creates pressure to cause fluid to exit the third cell.

In the above described operation of the cell assembly, the inlet lateral conduit of each cell is closed by the cell diaphragm upon movement of the diaphragm from one electrode to the other electrode. The vertical conduit of each cell is closed by the cell diaphragm upon movement of the diaphragm into contact with the electrode curved surface having the vertical conduit. When the voltages are applied to the electrodes the diaphragms move non linearly to produce a rolling actuation to thereby move the fluid from cell to succeeding cell.

In one embodiment, the mesopump sets are connected in series to produce a build up of pressure sequentially along the series. Alternatively or in addition, the sets may be connected in parallel to produce high throughput. One preferred embodiment includes as array wherein the sets are connected in three dimensional series/parallel arrays to produce a buildup of pressure and to produce high throughput.

These array type structures may be realized as a single unit or as an array of up to 100 parallel channels, so that pumping rates may be achieved from 10 ml/min to 10 l/min. By using electrostatic actuation the power consumption may be kept below 5 mV/channel and below 0.5 W per 100 channel array. The actuation voltages can be kept below 50 volts, particularly because of the specific shape of the electrodes. As an example, a 100 channel array will have a size of only one cubic inch.

Another embodiment contemplates the sets being connected in a tree-configuration for operation as a vacuum pump. Such a tree-configuration operates to reduce back streaming pressure without affecting pumping speed.

BRIEF DESCRIPTION OF THE DRAWINGS

For a more complete understanding of the invention, reference is hereby made to the drawings, in which:

FIG. 6 is a tree like serial connection in accordance with the present invention, with controlled backside pressure for compressor applications and the like;

DETAILED DESCRIPTION OF THE PREFERRED EMBODIMENT

The mesopumps of the present invention is best illustrated in terms of an array of elementary cells, where each cell includes a shaped chamber, a diaphragm and interconnecting conduits.

The mesopumps of the present invention are particularly advantageous because they may be manufactured from existing materials using existing manufacturing technologies. Thin film techniques already used for MEMS can be combined with existing polymer technology.

It should be noted that the particular combination of laminated and embossed polymer parts with high quality metal and dielectric thin films into three dimensional arrays of electrostatic actuators represents a completely new approach to actuator technology, embodying the best features of each technology. The electronics for driving the mesopumps of this invention are readily available, and voltages of less that 150 volts are in the ranges used for gas filled displays driven by conventional high voltage circuit technology.

Figure 1:
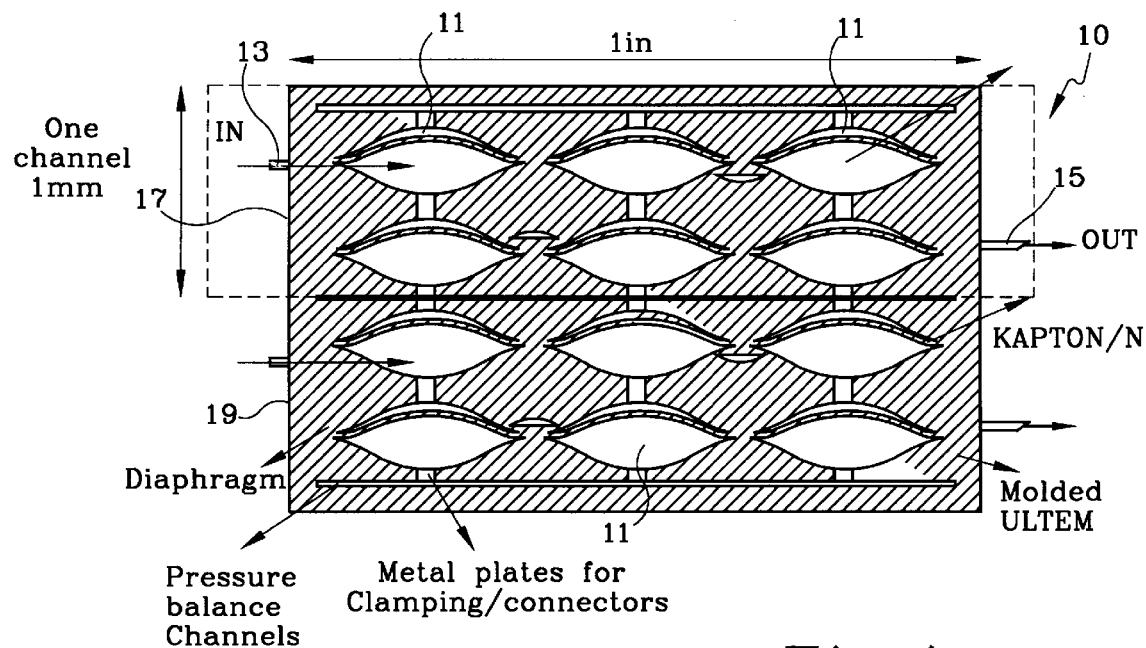
FIG. 1 is a schematic illustration of an electrostatically actuated mesopump, in accordance with the invention.

FIG. 1 illustrates a mesopump that has been fabricated in a one cubic inch configuration, and which uses the plurality of cells in series. The mesopump, 10 generally, consists of a plurality of cells 11 that efficiently and effectively transfer fluid from an inlet 13 to an outlet 15. This specific mesopump 10 has an upper channel 17 and a lower channel 19, arranged in parallel relationship, with both channels functioning in the same manner, in accordance with the invention.

The body 21 is constructed by molding a high temperature plastic such as ULTEM®, (registered trademark of General Electric Company, Pittsfield, Mass.), CELAZOLE®, (registered trademark of Hoechst-Celanese Corporation, Summit, N.J.), or KETRON®, registered trademark of Polymer Corporation, Reading, Pa.). The electrodes themselves can be formed by printing, plating, sputtering or EB deposition of metal followed by patterning by using dry film resist, as is known in the art. Low temperature organic and inorganic dialectic is used as an insulator between the actuating electrodes as shown below.

Figure 2:
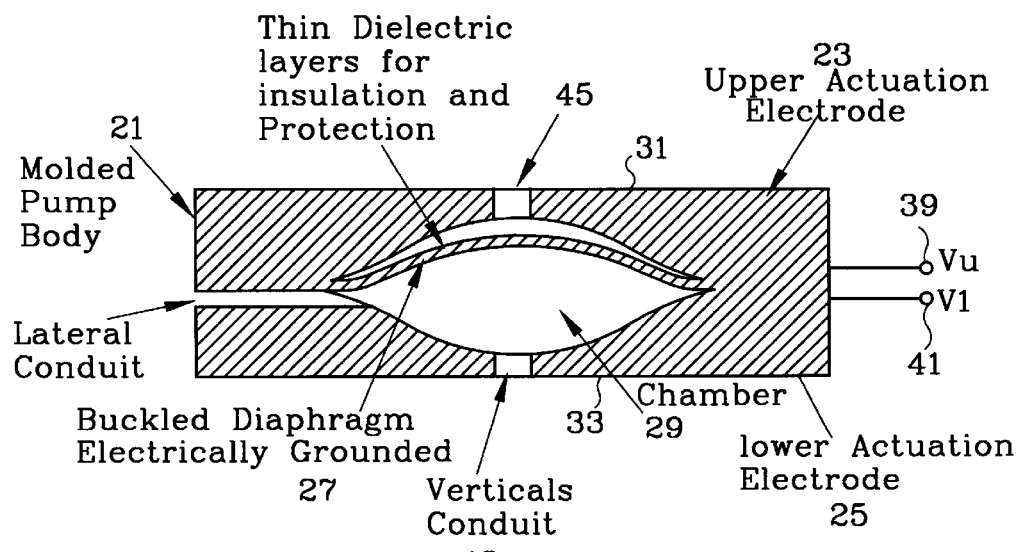
FIG. 2 is a an enlarged schematic view of one cell of the mesopump shown in FIG. 1.

As is more easily seen in FIG. 2, each channel 11 of the mesopump of FIG. 1 has a molded pump body 21 with an upper actuation electrode 23 and a lower actuation electrode 25. Body 21 also mounts an electrically grounded diaphragm 27 such that diaphragm 27 is capable of movement inside chamber 29 between upper electrode curved surface 31 and lower electrode curved surface 33. Body 21 also includes an inlet lateral conduit 35 and an outlet lateral conduit 37.

Diaphragm 27 conforms to curved surfaces 31 and 33 when it is electrostatically driven to one or the other surfaces through application of a voltage to the particular electrode via voltage source 39 for upper electrode 23 and voltage source 41 for lower electrode 25. Diaphragm 27 and the curved surfaces 31 and 33 are coated with thin dielectric layers (not shown) for electrical insulation and protection Mesopump body 21 also includes a vertical conduit 43 in curved surface 33 which permits material in chamber 29 between diaphragm 27 and the lower electrode 25 to be discharged when voltage is applied to move diaphragm into substantial contact with surface 33. Body 21 also includes a back pressure control conduit 45 in the upper electrode curved surface 31.

In the present invention, it is preferred that diaphragm be formed in a prebuckled shape, so that in the interim location between electrodes, the buckles compress and the shape is somewhat irregular. Upon movement to an electrode curved surface, the buckled diaphragm straightens out to form a smooth, uniform surface that fully engages the curved surface. Buckled diaphragms have a larger volume per stroke that can be obtained with reduced actuation force when compared to stretched or tensile loaded diaphragms. It is almost stress free in both of its stable positions, and this results in a system that is less sensitive to temperature variations or mismatches.

The diaphragm may be made from metal coated polymers such as KAPTON®, (registered trademark of E. I. du Pont de Nemours & Co., Wilmington, Del.), KALADEX® (registered trademark of ICI Films, Wilmington, Del.) and MYLAR® (registered trademark of E. I. du Pont de Nemours & Co., Wilmington, Del.), metal, or a conductive flexibly elastic polymer that permits it to conform its surface area to the curved surfaces. Both metal and elastic polymer diaphragms can be flat or buckled. Typically, the polymeric material have elastomeric properties sufficient to permit movement between said curved surfaces. For example, fabrication of the diaphragm is based upon technology developed for keyboard and flexible circuits that are produced in huge quantities, although not for mesopumps at this time, making the process well optimized. Preferred diaphragms are made from polymer films such as KAPTON® or MYLAR® (registered trademark of E. I. du Pont de Nemours & Co., Wilmington, Del.), or different polyesters that are commercially available.

Electrostatic actuation is not used in conventional diaphragm pumps because of the large distance (at least tens of microns) between the diaphragm and an electrode on the pump body. However, compared to alternative methods for moving the diaphragm (e.g., thermal, Lorentz force, pneumatic, motor-driven), electrostatic actuation is by far the most efficient actuation method in terms of power consumption and structural simplicity.

Electrostatic pressure is well known for its strong dependence on the spacing between the electrodes. It is given by:

$$P_{es} = \kappa \epsilon_o E^2 = \kappa \epsilon_o V^2 / d^2$$

where E is the electric field in the air gap between the diaphragm and the pump body and V and d are the corresponding voltage and distance.

For example, a voltage of 100 volts across a one micron thick film with a dielectric constant of 6 gives an electrostatic pressure of 5.2 atmospheres at the rolling contact point. In the structure shown herein, a high electrostatic pressure and a large displacement can be obtained at the same time, due to the special configuration that allows the diaphragm to roll against the chamber wall as described above. As voltage is applied, the point of high electrostatic pressure advances from the edge toward the center, producing rolling motion of the contact point on the cavity wall. One particular advantage of the present invention is that there is a minimal dead volume. As the diaphragm 27 moves from intimate contact with the upper curved surface 31 to the lower curved surface 33, all the air in the cavity is displaced. Thus it is easy to get chamber-to-channel volumes ratios (i.e., compression ratios) of up to 75 or more.

The dielectric material is a key element in the rolling contact electrostatic actuators. It must supply electrical isolation, passivation of the metal electrodes, low adhesion energy to prevent stiction, and a chemically stable surface. Dielectrics such as silicon dioxide and silicon nitride and materials known as Diamond Like Nanocomposites (DLN) are suitable dielectrics. These latter DLN materials have high dielectric strength, low surface energy and high corrosion resistance.

The high electrostatic pressure created between the diaphragm and the curved walls not only evacuates air from the cavity but also provides a sealing mechanism. The configuration of the access channels into the cavity allows this sealing capability to act as a built-in valve, providing high flow rectification. This is of particular advantage in applications where back streaming must be prevented, such as in vacuum pumps and compressors.

Figure 3:
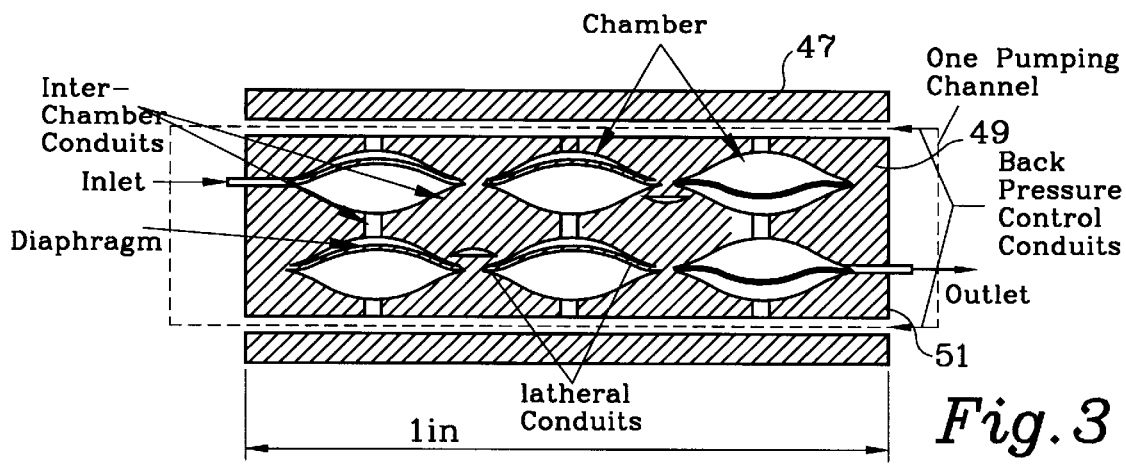
FIG. 3 is a schematic of one pumping channel of the mesopump shown in FIG. 1.

Pumping is accomplished by a series connection of a minimum of three chambers or cells working persistaltically. The arrangement of the cells as in pump 47 in FIG. 3 allows additional stages to be added in series. Each pumping channel in FIG. 3 consists of a stack of three flat rectangular plates with identical diaphragms between them. The top plate 49 and bottom plate 51 are identical, having on one side depressions for the cavities and slots, and holes for back pressure control on the other side. The middle plate 53 has depressions on both sides and also has slots and holes for the interconnecting conduits. The pump 47 in FIG. 3 is a parallel stacking of cells to provide increased pumping capability.

Figure 4:
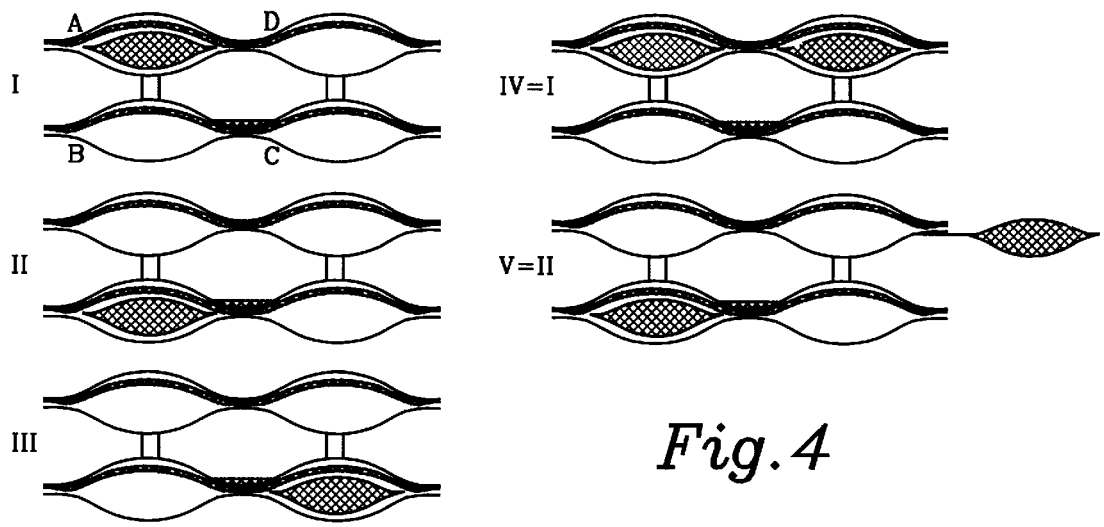
FIG. 4 is a schematic illustration of the operation of fluid flow through a single cell of the type shown in FIG. 2.

Operation of the mesopump as a peristaltic, positive displacement is shown in FIG. 4, where the diaphragm of chamber A moves up to thereby draw a fluid packet (such as a gas) into the lower part of chamber A through the lateral inlet. During the intake phase, the diaphragm of chamber B is acting as a valve, firmly closing the vertical conduit between chambers A and B. No backstreaming is allowed from the output. In the next phase, these two diaphragms move down together. As it rolls down on the lower wall of chamber A, the diaphragm of chamber A closes the intake conduit, acting as a valve and also pushes the fluid into chamber B. At the same time, displacement of the diaphragm of chamber B produces a recess in chamber B, drawing the fluid into this chamber. During this phase of the cycle, the diaphragm of chamber C keeps the lateral conduit between chambers B and C closed. Back streaming from the output is again prevented. In the third phase of the cycle, the diaphragm of chamber A keeps the conduits toward chamber B and toward the input firmly closed, while the diaphragms of chambers B and C are forcing the fluid packet into chamber C. In this way a basic pumping cycle is completed. This cycle is repeated to move the gas packet through whatever series or parallel combination of cells have been arranged.

Figure 5:
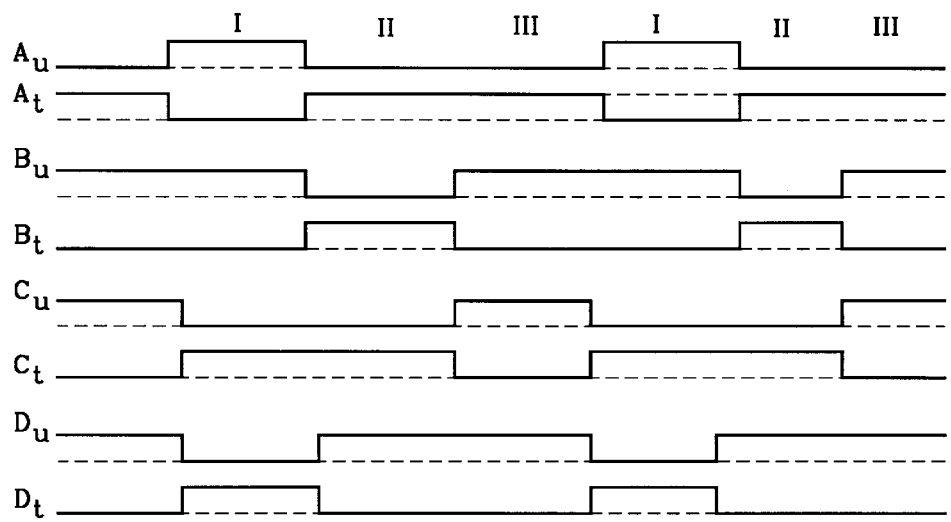
FIG. 5 is a schematic diagram of the voltage applied to one electrode in the pumping cycle shown in FIG. 4.

FIG. 5 illustrates the driving voltages applied to the upper (u) and lower (l) electrodes of each chamber in the phases of the pumping cycle described above with reference to FIG. 4.

One advantage of the present invention is that the diaphragm is subjected to a snapping action as it converts from contact with one electrode curved surface to the other. Test analyses were run for a nominal 10 mm diameter by 25 $\mu$m thick diaphragm with 75 $\mu$m deep upper and lower chambers. The expected rolling action was observed. As voltage was increased, the diaphragm-electrode contact begins at the outer perimeter and moves in toward the center, with complete diaphragm contact at 50 volts. There was a snapping action evident between 48 and 50 volts, and is due to the nonlinear, position dependent force as well as the bistable nature of the diaphragm. Electrostatic force is proportional to the square of the actuation voltage, so it is expected that the required actuation voltage would vary as the square root of voltage, and this behavior has been found to be roughly correct.

Figure 6:
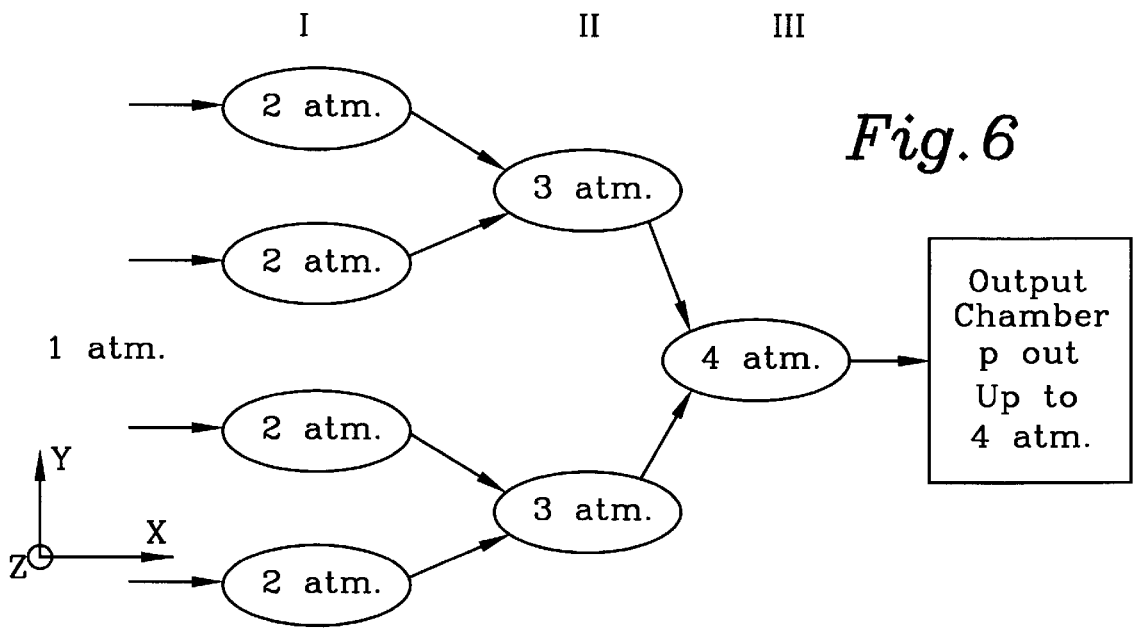

The present invention may also be placed in a tree-type arrangement, shown in FIG. 6. This provides increased capability for applications that require large pressure differences and back pressure control. To fully realize the advantages of serial connection, the back pressure on the diaphragms in each stage has to be correspondingly controlled. FIG. 6 illustrates a tree like serial connection of cells with controlled backside pressure, with the quantities in the circles representing backside pressures. This embodiment contemplates connection of the backsides of all diaphragms in a system of chambers having pressures that vary between the output pressure and the input pressure, such that no more than one atmosphere appears across any diaphragm. During the first cycles on the tree like serial connection, flow will be limited by the pumping capacity of the final stages. After a number of cycles, the pressure in the output chamber of the last cell in the series will increase, thereby increasing the pressure on the back side of the diaphragms and producing an increase in the flow rate, until the pumping capacity of the input stage is reached.

The present invention is also capable of producing a vacuum pump for vacuums in the millitorr range by connecting cells to be fabricated in three-dimensional series/parallel arrays. Series operation allows the build up of significant pressure ratios while parallel operation provides high throughput. The device of FIG. 6 may also be used as a vacuum pump, but backside pressure is no longer an issue as the diaphragms can work against one atmosphere pressure. This configuration also has the capability to reduce the back streaming pressure without affecting pump speed for a given pump size.

Figure 7:
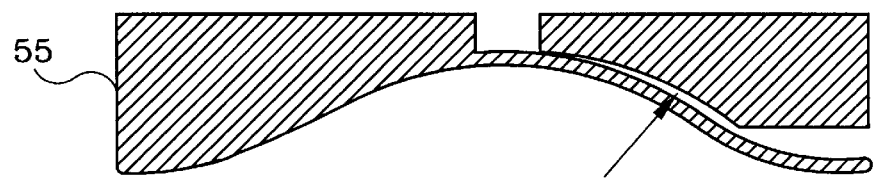
FIG. 7 is an enlarged cut-away section of the cell shown in FIG. 2, illustrating a preferred embodiment of the invention.

Turning now to FIG. 7, an embodiment is shown that insures proper evacuation of fluid from the second chamber, such as chamber B of FIG. 4, into a third chamber, such as chamber C again of FIG. 4. The upper electrode 55 shown in FIG. 7 includes a shallow channel 57 between electrode 55 and diaphragm 59 that leads to the evacuation channel between chambers B and C of FIG. 4, for example.

Figure 8:
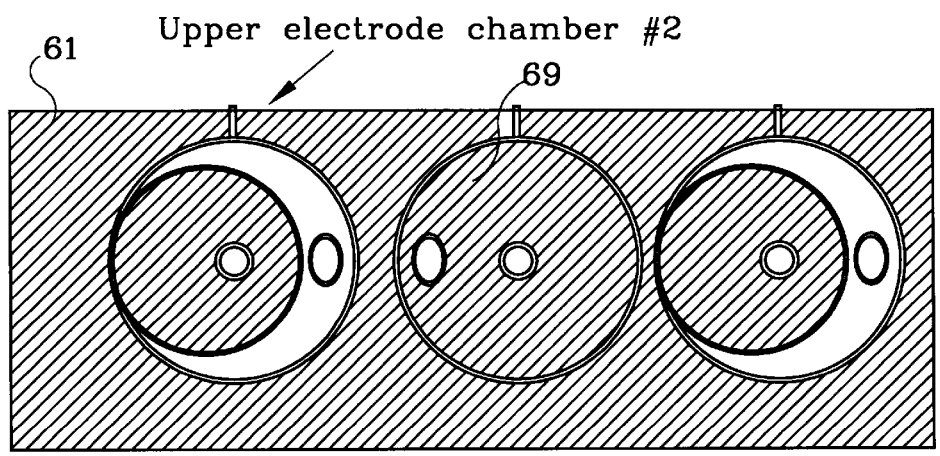
FIG. 8 is a schematic illustration of the electrode pattern for the cell section shown in FIG. 9.

An alternative means for improved evacuation of such a second chamber is shown in FIG. 8, where an upper chamber 61 contains curved electrode surfaces that are slightly oval in shape, at 63.

The mesopumps of the present invention have a wide variety of applicability-end uses. In the military, a variety of missions require detection of chemical and biological agents and explosives. These include battlefield warning, counter proliferation and treaty monitoring. Detection technology is needed for rapid identification and quantification of the entire suite of chemical and biological agents, as well as the detection of precursors, degradation products and solvents associated with their manufacture and distribution. The present invention provides sensor technology that is sufficiently sensitive and low enough in power and cost to be available for use with a variety of ongoing programs. Among these are enzyme-based electrochemical sensors, aerosol collectors to monitor aerosol sizes and concentrations using cascade impactors, UV- induced fluorescence-based sensors for biological detection and chemical sensors for detection of volatile organic compounds in explosives and chemical agents. Biological species identification based on DNA techniques have been demonstrated using the polymerase chain reaction and capillary electrophoresis.

The present invention is also admirably suited for use with mass spectrometers and other vacuum-based instruments in compact fieldable detection systems because, for the first time, vacuum pumps are available that are compatible in size, weight and power with the rest of the instrument. Also now possible for the first time are mesoscopic compressors made in accordance with the present invention that are suitable for miniature refrigeration or cooling systems, or to pressurize pneumatic chambers for microfluid handling systems, such as a fieldable DNA analysis system that might include metering, sample filtration, PCR reagent injection and sample/reagent transport.

While particular embodiments of the present invention have been illustrated and described, it is not intended to limit the invention, except as defined by the following claims.

I claim:

1. A mesopump having a plurality of elementary cells, each of said cells comprising:

a body forming an electrode cavity having an upper electrode and a lower electrode, each of said electrodes having a curved surface facing toward the curved surface of the other electrode to define said cavity, said body including electrical activation means for selectively energizing said electrodes;

a bistable diaphragm mounted and grounded in said body and having a major portion located in said cavity between said curved surfaces, said diaphragm being adapted to deflect toward said upper and lower electrode curved surfaces to conform thereto;

lateral conduit means in said body forming an end conduit, said lateral conduit means being operably connected to the portion of said diaphragm mounted in said body and positioned to be opened and closed by movement of said diaphragm for controlling flow of fluid through said end conduit;

vertical conduit means operatively connected to at least one curved surface of an electrode cavity for controlling flow of fluid there through by movement of said diaphragm into and out of contact with said vertical conduit means; and interconnecting conduit means for connecting said cell to said plurality of cells to form said mesopump;

whereby activation of said electrodes causes movement of said diaphragm between said curved surfaces of said electrodes to move fluid into and out of said body.

2. The mesopump of claim 1, wherein said cells further include a vertical back pressure control conduit on the opposite electrode and on the other side of said diaphragm from said vertical conduit means.

3. The mesopump of claim 1, wherein said diaphragm is formed from buckled metal to increase its surface area and permit stable alignment with said curved surfaces.

4. The mesopump of claim 1, wherein said diaphragm is flexibly elastic to conform its surface area to said curved surfaces.

5. The mesopump of claim 4, wherein said diaphragm is formed from a polymeric material having elastomeric properties sufficient to permit movement between said curved surfaces.

6. The mesopump of claim 1, wherein movement of said diaphragm from the curved surface of one electrode to the curved surface of the other electrode cooperates with said lateral conduit means to open one of said inlet end conduit and outlet end conduit and closing the other of said inlet end conduit and outlet end conduit.

7. The mesopump of claim 1, which includes a plurality of sets of elementary cells, said sets each comprising:

a first cell having an inlet end lateral conduit means, said inlet end lateral conduit means being connected to a source of fluid, said first cell having a fluid outlet formed by its vertical conduit means;

a second cell connected to said first cell vertical conduit means by a second cell vertical conduit means as its inlet source and having an outlet end lateral conduit means as its fluid outlet; and a third cell connected to said second cell outlet end lateral conduit means at an inlet end lateral conduit means and having a fluid outlet formed by its outlet end lateral conduit means.

8. The mesopump of claim 7, which further includes:

a fourth cell connected to said third cell outlet vertical conduit means by its vertical conduit means as its inlet source and its outlet end lateral conduit means is its fluid outlet;

a fifth cell having an inlet end lateral conduit means, said inlet end lateral conduit means being connected said fluid outlet of said fourth cell, said fifth cell having a fluid outlet formed by its vertical conduit means; and a sixth cell connected to said fifth cell vertical conduit means by a sixth cell vertical conduit means as its inlet source and having an outlet end lateral conduit means as its fluid outlet.

9. The mesopump of claim 7, wherein said sets are connected in series to produce a build up of pressure sequentially along said series.

10. The mesopump of claim 7, wherein said sets are connected in parallel to produce high throughput.

11. The mesopump of claim 7, wherein said sets are connected in three dimensional series/parallel arrays to produce a buildup of pressure and to produce high throughput.

12. The mesopump of claim 7, wherein said sets are connected in a tree-configuration to reduce back streaming pressure without affecting pumping speed.

13. The mesopump of claim 12, wherein said tree-configuration operates for operation as a vacuum pump.

14. A method of pumping fluids using the mesopump of claim 7, comprising the steps of:

applying a voltage between a grounded diaphragm and an upper electrode of said first and second cells, whereby suction is created to cause fluid to enter through said first cell inlet lateral conduit;

switching voltage to the lower electrodes of said first and second cells, whereby fluid moves to said second cell through its second cell vertical conduit; and switching voltage back to the upper electrode in said second cell and applying voltage to said upper electrode in said third cell to transfer fluid through said second cell outlet end lateral conduit means into said third cell through said third cell inlet end lateral conduit means and expel fluid from said third cell through its outlet end lateral conduit means.

15. The method of claim 14, wherein said inlet lateral conduit of each cell is closed by said cell diaphragm upon movement of said diaphragm from one electrode to the other electrode.

16. The method of claim 14, wherein said vertical conduit of each cell is closed by said cell diaphragm upon movement of said diaphragm into contact with the electrode curved surface having said vertical conduit.

17. The method of claim 14, wherein said voltages are applied to said electrodes in an amount sufficient to cause said diaphragms to move non linearly to produce a rolling actuation to thereby move said fluid from cell to succeeding cell.

* * * * *